(12) United States Patent
Oliver et al.

(10) Patent No.: US 7,441,465 B2
(45) Date of Patent: Oct. 28, 2008

(54) MEASUREMENT OF PROPERTIES OF THIN SPECIMENS BASED ON EXPERIMENTALLY ACQUIRED FORCE-DISPLACEMENT DATA

(75) Inventors: Warren C. Oliver, Knoxville, TN (US); Erik G. Herbert, Knoxville, TN (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/757,076

(22) Filed: Jun. 1, 2007

(65) Prior Publication Data

US 2007/0295091 A1  Dec. 27, 2007

Related U.S. Application Data

(60) Provisional application No. 60/810,374, filed on Jun. 2, 2006.

(51) Int. Cl.
*G01N 3/00* (2006.01)
(52) U.S. Cl. ............... 73/808; 73/760; 73/763; 73/774; 73/781; 73/788; 73/789; 73/790; 73/796
(58) Field of Classification Search ............. 73/760, 73/763, 774, 781, 788, 789, 790, 796, 808
See application file for complete search history.

(56) References Cited

U.S. PATENT DOCUMENTS

| | | | |
|---|---|---|---|
| 3,854,328 A | 12/1974 | Schmidt | |
| 3,927,558 A | 12/1975 | Philippe et al. | |
| 3,958,450 A | 5/1976 | Kleesattel | |
| 3,994,158 A * | 11/1976 | Weinhold | 73/798 |
| 4,084,322 A | 4/1978 | Albertazzi | |
| 4,297,884 A | 11/1981 | Leveque et al. | |
| 4,475,403 A | 10/1984 | Lentz | |
| 4,478,086 A | 10/1984 | Gram | |
| 4,848,141 A | 7/1989 | Oliver | |
| 4,869,111 A | 9/1989 | Ohya et al. | |

(Continued)

FOREIGN PATENT DOCUMENTS

FR  2680003 A1  8/1991

(Continued)

OTHER PUBLICATIONS

Michael S. Baker, et al., Integrated Measurement-Modeling Approaches for Evaluating Residual Stress Using Micromachined Fixed-Fixed Beams, Journal of Microelectromechanical Systems, vol. 11, No. 6, Dec. 2002, pp. 743-753.

(Continued)

*Primary Examiner*—Edward Lefkowitz
*Assistant Examiner*—Freddie Kirkland, III

(57) ABSTRACT

A method and system are provided for obtaining force-displacement responses for a specimen or sample of material. The sample is supported with a spanning portion spanning in an environment between at least three points not in a line, wherein the points are fixed relative to each other, and wherein the spanning portion is capable of displacement relative to the points. An oscillating mechanical excitation at at least one frequency and at at least one known amplitude is applied to the spanning portion. In addition, at least one other mechanical excitation is also applied to the spanning portion independently of the oscillating mechanical excitation.

41 Claims, 6 Drawing Sheets

U.S. PATENT DOCUMENTS

| | | | |
|---|---|---|---|
| 4,877,957 | A | 10/1989 | Okada et al. |
| 5,195,378 | A | 3/1993 | Ferguson |
| 5,224,386 | A | 7/1993 | Curtis .................. 73/833 |
| 5,361,640 | A | 11/1994 | Carroll et al. ............ 73/831 |
| 5,425,276 | A * | 6/1995 | Gram et al. .............. 73/816 |
| 5,693,890 | A | 12/1997 | Holmes ................. 73/856 |
| 5,719,339 | A | 2/1998 | Hartman et al. ........... 73/811 |
| 6,026,677 | A * | 2/2000 | Bonin ................... 73/105 |
| 6,247,355 | B1 * | 6/2001 | Suresh et al. ............. 73/82 |
| 6,679,124 | B2 | 1/2004 | Oliver |
| 6,732,591 | B2 * | 5/2004 | Miles et al. ............. 73/808 |
| 6,844,721 | B2 * | 1/2005 | Oliver .............. 324/207.17 |
| 2002/0017146 | A1 * | 2/2002 | Oliver .................. 73/856 |
| 2002/0162400 | A1 | 11/2002 | Xie et al. |
| 2003/0016007 | A1 * | 1/2003 | Oliver .............. 324/207.17 |
| 2006/0016996 | A1 | 1/2006 | Kaneko et al. |
| 2006/0186874 | A1 | 8/2006 | Mackin et al. |

FOREIGN PATENT DOCUMENTS

| | | |
|---|---|---|
| WO | WO 03/098193 | 5/2003 |

OTHER PUBLICATIONS

H.D.Espinosa, et al., Fracture strength of ultrananocrystalline diamond thin films-identification of Weibull parameters, Journal of Applied Physics, vol. 94,No. 9, Nov. 1, 2003, pp. 6076-6084.

H.D. Espinosa et al., A New Methodology to Investigate Fracture Toughness of Freestanding MEMS and Advanced Materials in Thin Film Form, Feb. 2005, Journal of Microelectromechanical Systems, vol. 14, No. 1, pp. 153-159.

Meyers, Marc A., "Introduction to Mechanical Testing" in Metals Handbook®: American Society for Metals, edited by Boyer and Gall, 34.1-34.4, Metals Park, OH: American Society for Metals, 1985.

Pethica, J.B. and W.C. Oliver, "Mechanical Properties of Nanometre Volumes of Material: Use of the Elastic Reponse of Small Area Indentations" Materials Research Society Symposium Proceedings 130, 13-23, 1989.

Oliver, W.C. and G.M. Pharr, "An improved technique for determining hardness and elastic modulus using load and displacement sensing identation experiments" Journal of Materials Research, vol. 7, No. 6, 1564-1583, 1992.

Report prepared by D. Read, "Piezo-Actuated Microtensile Test Apparatus" Materials Reliability Division of the National Institute of Standards and Technology, Boulder, CO, pp. 255-259, circa 1996.

Lucas, B.N., W.C. Oliver and J.E. Swindeman, "The Dynamics of Frequency-Specific, Depth-Sensing Indentation Testing" Reprinted from Materials Research Society, Symposium Proceedings: Fundamentals of Nanoindentation and Nanotribology, vol. 522, Eds. Baker, S.P., N.A. Burnham, W.W. Gerberich and N.R. Moody).

H.D. Espinosa, et al., Elasticity, Strength and Toughness of Three Novel MEMS/NEMS Materials-3C-SiC,UNCD,ta-C, Journal of Microelectromechanical Systems, 2005.

Nanomechanical testing of circular freestanding polymer films with sub-micron thickness, Kyle C. Maner et al, Nano-Innovation Center, MTS Instruments, Oak Ridge, TN 37830, USA Structural and Solid Mechanics Group, Department of Civil Engineering, University of Virgina, Charlottesville, VA 22904, USA ᶜDepartment of Materials Science and Engineering, University of Virgina, Charlottesville, VA 22904, USA Recieved May 7, 2004; revised Jul. 15, 2004; accepted Jul. 23, 2004.

Indentation of freestanding circular elastomer films using spherical indenters. Acta Materialia, vol. 52, Issue 16, pp. 4877-4885 O. Scott, M. Begley, U. Komaragiri, T. Mackin.

An investigation into DMTA clamping problems, Leonard T.; Gooberman G., *Meausrement Science and Technology*, vol. 3, No. 3, 1992, pp. 1992, pp. 275-282(8), Institute of Physics Publishing.

Official Search Report and Written Opinion of the European Patent Office in counterpart foriegn application No. PCT/us2007/012944 filed Jun. 1, 2007.

Nanomechanical testing of circular freestanding polymer films with sub-micron thickness, Kyle C. Maner et al, Nano-Innovation Center, MTS Instruments, Oak Ridge, TN 37830, USA Structural and Solid Mechanics Group, Department of Civil Engineering, University of Virgina, Charlottesville, VA 22904, USA ᶜDepartment of Materials Science and Engineering, University of Virgina, Charlottesville, VA 22904, USA Recieved May 7, 2004; revised Jul. 15, 2004; accepted Jul. 23, 2004.

Indentation of freestanding circular elastomer films using spherical indenters. Acta Materialia, vol. 52, Issue 16, pp. 4877-4885 O. Scott, M. Begley, U. Komaragiri, T. Mackin.

An investigation into DMTA clamping problems, Leonard T.; Gooberman G., *Meausrement Science and Technology*, vol. 3, No. 3, 1992, pp. 1992, pp. 275-282(8), Institute of Physics Publishing.

Official Search Report and Written Opinion of the European Patent Office in counterpart foriegn application No. PCT/us2007/012944 filed Jun. 1, 2007.

Spherical indentation of freestanding circular thin films in the membrane regime Matthew R. Begley et al., Structural and Solid Mechanics Program, Department of Civil Engineering, University of Virgina, Charlottesville, Va 22904, USA, Department of Mechanical and Industrial Engineering, University of Illinois at Urbana-Champaign, Urbana, IL 68102, USA Received Jan. 14, 2004; Revised Mar. 2, 2004; accepted Mar. 3, 2004.

\* cited by examiner

US 7,441,465 B2

MEASUREMENT OF PROPERTIES OF THIN SPECIMENS BASED ON EXPERIMENTALLY ACQUIRED FORCE-DISPLACEMENT DATA

CROSS-REFERENCE TO RELATED APPLICATION

The present application is based on and claims the benefit of U.S. provisional patent application Ser. No. 60/810,374, filed on Jun. 2, 2006, the content of which is hereby incorporated by reference in its entirety.

BACKGROUND

The discussion below is merely provided for general background information and is not intended to be used as an aid in determining the scope of the claimed subject matter.

The use of indenters to obtain data indicative of mechanical properties of test specimens is known. U.S. Pat. No. 4,848,141 describes a method for continuously measuring the elastic response of a mechanical junction between an indenter and a sample material by applying a predetermined increasing direct force to said indenter to load the junction while applying a relatively small amplitude oscillatory force to the junction of sufficient magnitude to alternately load and unload the junction while continuously measuring both the amplitude and phase of the resulting displacement of the indenter relative to the applied oscillatory force as a continuous indication of the stiffness of the junction as the indenter is forced against the sample in a process of measuring various other mechanical properties of the sample material.

This patent further describes a method to measure stiffness (i.e., elastic and inelastic response) of a sample material in an indentation test system, wherein an indenter probe is forced into contact with the sample over a loading and unloading cycle, as the indentation process is carried out without interrupting the continuity of the process. This is made possible by superimposing a relatively high frequency AC signal source onto a DC signal used to drive a force generating means that applies the force to the indenter probe. The DC driving force is a very slow changing applied force. The AC driving force is sized such that a displacement amplitude (typically 10 Angstroms prior to contact) results. The force alternates at a selected frequency which can range from about 0.5 Hz to 1 MHz (megahertz) depending on the mechanics of the indenter probe assembly and the capabilities of the detection electronics. The alternating displacement component of the signal taken from a displacement gage is monitored by a frequency specific amplifier which also determines the phase of the signal relative to the applied AC drive signal. This provides a measure of the slope of the unloading versus displacement curve, i.e., continuous measurement of the elastic load/displacement response of the contact of the indenter with the sample. This approach yields the desired measurement of stiffness without significantly changing the DC force component acting on the junction. Using this method, a direct, virtually instantaneous and continuous measure of stiffness of the contact junction between the indenter and the sample is obtained as a function of the oscillatory displacement of the indenter probe tip during the process of loading and unloading the indenter and sample junction, i.e., as plastic deformation of the sample occurs.

Although the foregoing is useful in measuring stiffness of contact for a sample subjected to indentation, other specimens such as thin films have other material characteristics that need to be measured, but are unsuited for this type of testing. In particular, there is a need to measure or obtain relationships of properties of thin films such as but not limited to the elastic modulus and residue stress.

SUMMARY

This Summary and Abstract are provided to introduce some concepts in a simplified form that are further described below in the Detailed Description. This Summary and Abstract are not intended to identify key features or essential features of the claimed subject matter, nor are they intended to be used as an aid in determining the scope of the claimed subject mailer. In addition, the description herein provided and the claimed subject matter should not be interpreted as being directed to addressing any of the short-comings discussed in the Background.

A method and system are provided for obtaining force-displacement responses for a specimen or sample of material. From the force-displacement response an indication of at least one mechanical property of the material from which the sample is made can be obtained.

Generally, the sample is supported with a spanning portion spanning in an environment between at least three points not in a line, wherein the points are fixed relative to each other, and wherein the spanning portion is capable of displacement relative to the points. In one exemplary embodiment, the sample is supported on opposite ends, where one end comprises at least two points and the other end comprises at least one additional point, where such points do not lie in a line. However, it should be noted this is but one manner in which a spanning portion may be supported.

An oscillating mechanical excitation at at least one frequency and at at least one known amplitude is applied to the spanning portion. In addition, at least one other mechanical excitation is also applied to the spanning portion independently of the oscillating mechanical excitation. The force-displacement responses are obtained from these excitations. In particular, a first force-displacement response of the spanning portion of the sample relative to the applied oscillating mechanical excitation is obtained, and a second force-displacement response of the spanning portion of the sample relative to the at least one other mechanical excitation is also obtained. From this data, an indication of at least one mechanical property of the material from which the specimen is made based on the force-displacement responses can be obtained.

DETAILED DESCRIPTION

Figure 1:
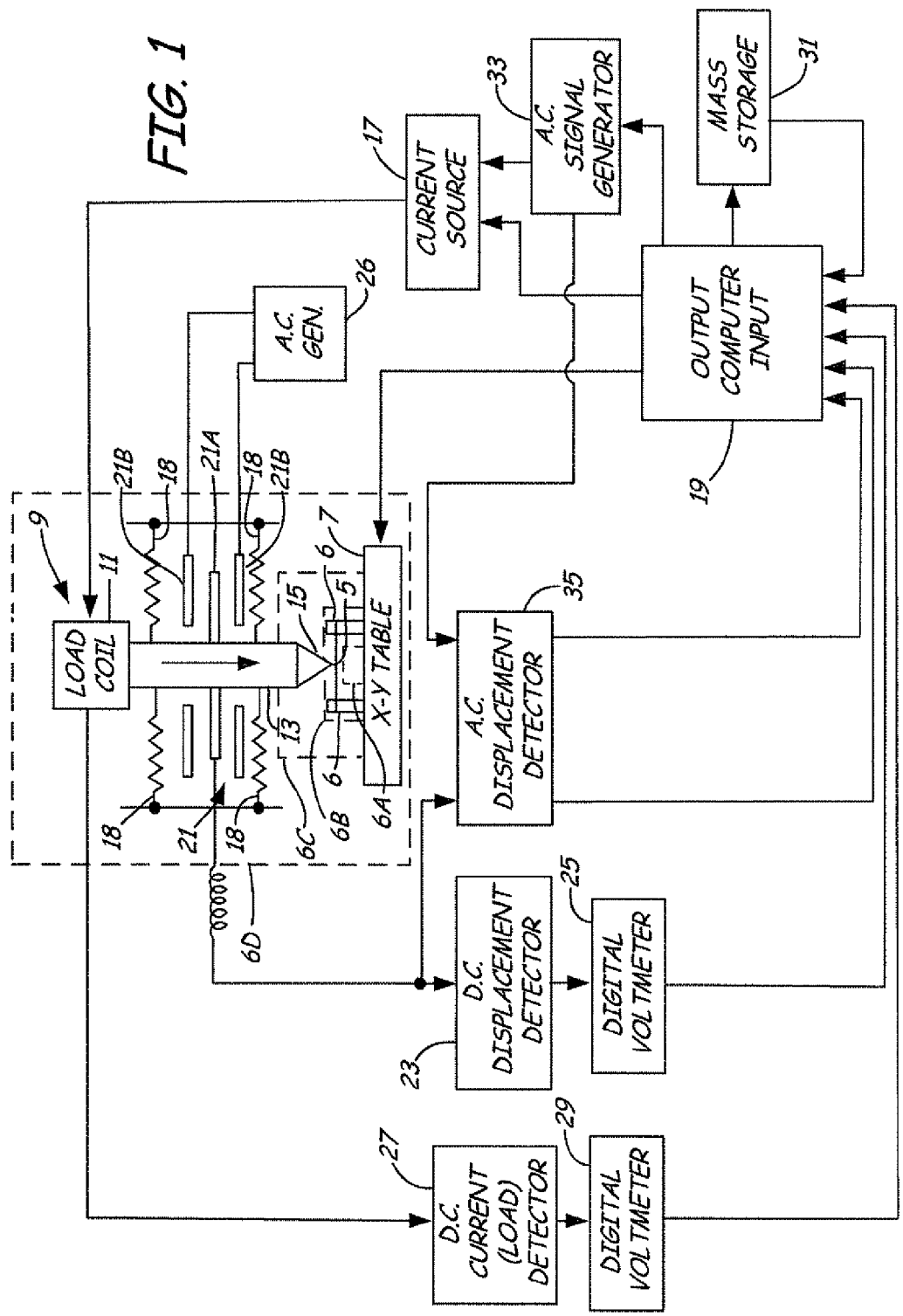
FIG. 1 is a schematic diagram of an exemplary system for applying loads to a sample.

Referring to FIG. 1, there is shown a schematic diagram of an exemplary system for obtaining force-displacement responses for a specimen or sample of material 5. From the force-displacement response an indication of at least one mechanical property of the material from which the sample is made can be obtained.

Figure 7:
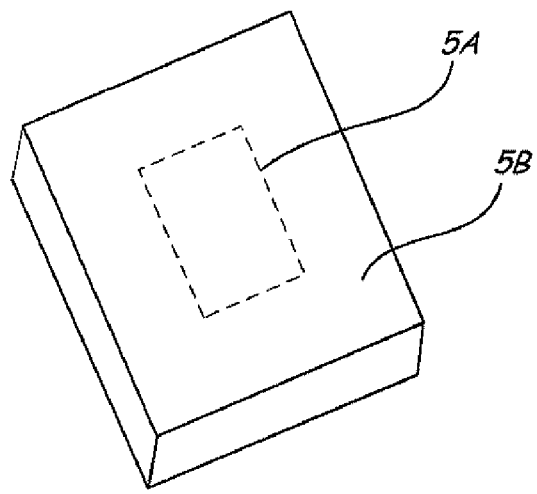
FIG. 7 is a perspective view of another sample.

Generally, the sample 5 is supported with a spanning portion 5A spanning in an environment between at least three points not in a line, wherein the points are fixed relative to each other, and wherein the spanning portion 5A is capable of displacement relative to the points. In the exemplary embodiment, the sample 5 is supported on opposite ends, where one end comprises at least two points and the other end comprises at least one additional point, where such points do not lie in a line. However, it should be noted this is but one manner in which a spanning portion may be supported. For instance, in another embodiment, the spanning portion 5A may be supported about a portion, or all of its perimeter such as with a frame 5B as illustrated in FIG. 7.

An oscillating mechanical excitation at at least one frequency and at at least one known amplitude is applied to the spanning portion 5A. In addition, at least one other mechanical excitation is also applied to the spanning portion 5A independently of the oscillating mechanical excitation.

As indicated above, force-displacement responses are obtained. In particular, a first force-displacement response of the spanning portion 5A of the sample 5 relative to the applied oscillating mechanical excitation is obtained, and a second force-displacement response of the spanning portion 5A of the sample 5 relative to the at least one other mechanical excitation is also obtained. From this data, an indication of at least one mechanical property of the material from which the specimen is made based on the force-displacement responses can be obtained.

The force-displacement responses can be obtained using either force or displacement control. In particular, force can be the controlled variable of the oscillating mechanical excitation, where the resulting displacement to the applied force is then measured. In an alternative embodiment, displacement can be the controlled variable of the oscillating mechanical excitation, where the force necessary for the desired displacement is then measured. Similarly, and independently of the manner in which the oscillating mechanical excitation is controlled, force can be the controlled variable of the other mechanical excitation, where the resulting displacement to the applied force is then measured. Likewise, in an alternative embodiment, displacement can be the controlled variable of the oscillating mechanical excitation, where the force necessary for the desired displacement is then measured.

With respect to the oscillating mechanical excitation, a plurality of frequencies each having a selected amplitude can be applied. The plurality of frequencies can be applied simultaneously (i.e. superimposed on each other) or they can be applied sequentially, either at different discrete frequencies or constantly changing in a sweeping manner over a selected range of frequencies. Furthermore, one or more of the amplitudes can vary over a selected time period.

With respect to the other mechanical excitation, a static force or displacement can be applied for a selected time period. However, if desired, the amount of force or displacement can also vary over time either increasing or decreasing such as following a selected ramping function.

Figure 2:
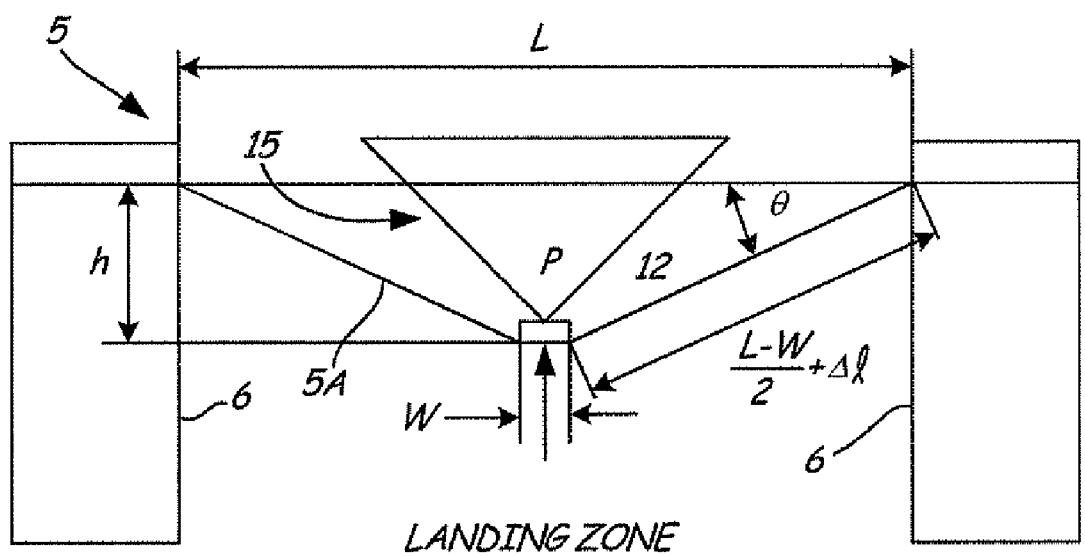
FIG. 2 is an enlarged schematic diagram of the sample, support structure and engaging member.

Referring now to the exemplary embodiment illustrated in FIGS. 1 and 2, the sample 5 is supported at opposite ends using supports 6 that in turn can be mounted on a computer controlled X-Y table 7 so that the sample 5 can be positioned in a known position. In this embodiment, the surface to be engaged faces up; however in another embodiment the surface to be engaged can also face downwardly or to the side.

An engaging tip or probe 15 is provided which is herein positioned over the sample 5, but in other embodiments can be placed below or to the side of the sample 5 to engage the surface as mentioned above. The tip 15 is displaced relative to the support system, for example, the fixed ends of the sample 5 (i.e. supports 6) so as to apply a load, for example, as illustrated in FIG. 2. As appreciated by those skilled in the art, such relative movement can be caused by movement of the tip 15, movement of the supports 6, or movement of both the tip 15 and the supports 6. An actuator assembly coupled to the supports 6 and/or tip 15 can be provided to cause such movement. The actuator assembly can be hydraulic, pneumatic, magnetic and/or electric (e.g. electrostatic, electromagnetic, and/or piezoelectric).

In the exemplary embodiment, the spanning portion 5A is disposed in a fluid (i.e., air); however, this is but one embodiment. If desired, the spanning portion 5A, with possibly other portions of the sample 5, or the entire sample 5, can be disposed in any other fluid (gas and/or liquid) as may be desired. In such cases, it may be helpful to provide a suitable container for the fluid such as any one or more of containers 6A, 6B, 6C or 6D (schematically illustrated), depending on the type of fluid (at least one gas and/or at least one liquid) constituting the environment. Typically, the fluid surrounding the sample portion under test does not impart significant stress on to the spanning portion 5A when the spanning portion 5A is displaced. If desired, other environmental parameters such as but not limited to temperature, pressure, humidity can also be adjusted using well known equipment.

In the exemplary embodiment, an actuator assembly 9 includes an actuator device, herein by example a current driven load coil 11 activated by the application of electrical current from a computer controlled variable current source 17, to move a rod 13 having the tip 15 downward into engagement with the sample 5. The actuator assembly 9 is supported by leaf springs 18 which constrain it to move only in a direction normal to the sample 5 surface. Once the tip 15 contacts the sample (directly or indirectly) a preselected force and/or displacement pattern is applied to the actuator device by the programmed variation of the current applied to the drive coil 11. Although illustrated herein where the engaging end pushes on the sample 5, in a further embodiment, the actuator assembly 9 can be arranged to pull on the sample 5, for example, with a suitable element bonded to the sample 5 to which the engaging end 15 can be coupled.

Referring to FIG. 2, the engaging end tip 15 may be in the form of a typical triangular pyramidal diamond engaging end that engages a landing pad 12 secured to a surface of the sample 5. If a pyramidal tip, or other suitable shape having a single contact tip, is used it can be advantageous to contact the landing pad 12 in the center thereof so as to spread the force uniformly across the width of the sample 5. In yet another embodiment, the engaging end tip 15 can have multiple points of contact such as in the form of a line or knife edge. With an engaging end tip 15 in the form of a line or edge, the engaging end tip 15 can be of length so as to extend beyond the longitudinal edges of the sample 5 across the width thereof so as to prevent curling of the sample 5. However, care should be typically taken so as to position the engaging end tip 15 such that the contact edge of the engaging end tip 15 is parallel to a plane of the surface of the landing pad 12 or the sample 5 so that contact of the engaging end tip 15 across the width is made at the same time. As appreciated by those skilled in the art, other geometries for the tip 15 can be used such as a tip having an end in the shape of an arc or cylinder.

In an alternative embodiment, it may be useful to induce torsional loading in the sample in addition, or in the alternative, to the tensile loading. Torsional force-displacement data can be used to determine shear modulus or Poisson's ratio. For example, torsional loading can be obtained by applying point loading at various positions across the width of the sample (i.e. off center), which would induce torsional loading in the sample. Generally, the geometry of the tip 15, the shape of the loading pad 12 on the spanning portion 5A, and the manner in which the tip 15 engages the loading pad 12 can be adjusted to induce a variety of desired stress states in the spanning portion 5A.

In the embodiment illustrated, the current source 17 is controlled by the system computer 19, which can also control the X-Y table 7. The displacement of the engaging end 15 is measured by a sensor such as a capacitive displacement gage 21, whose output is connected to a DC displacement detector 23. The detector 23 digitizes the DC displacement signal which is fed through a digital voltmeter 25 to an input of the computer 19. The voltmeter 25 provides a calibrated readout of the engaging end displacement to an operator during testing procedures. As known in the art, a center plate 21A is coupled to the rod 13 to move therewith. The center plate 21A moves relative to drive plates 21B (which are circular having apertures through which rod 13 can extend), which are driven by typically an AC source 26. In the embodiment illustrated, the springs 18 are separate from the center plate 21A; however, in another embodiment, the springs can also, or in the alternative, be formed as part of the center plate 21A.

At this point it should be noted rod 13 can comprise an inner rod (not shown) that is connected to the actuator assembly 9 at a first end and the tip 15 at a second end. An outer tube, spaced apart from the inner rod is joined at a first end to the tip 15 and the center plate 21A.

Furthermore, as appreciated by those skilled in the art, capacitive displacement gage 21 is but one form of high precision displacement sensor that can be used. For example, other types of displacement sensors include, but are not limited to, those that are based on electromagnetic radiation such as laser interferometers, fiber optic based sensors or radar, magnetically based or other forms of electric based sensors such as strain gages. In addition, any form of sensor used in or suitable for an atomic force microscope could be used.

The force applied to the sample through the engaging end 15 can be monitored. In this embodiment, a DC current detector 27 senses the DC drive current applied to the load coil 11. The DC load current is digitized by the detector 27 and fed through a second digital voltmeter 29 to a further input of computer 19. The computer may be connected to a mass storage device 31 in which data and system operating parameters are stored.

Using the system as described above, a sample 5 is mounted to supports 6 positioned at a known location via the X-Y table 7 and the programmed computer 19 is signaled to start the test procedure. The computer is programmed to apply a prescribed force, single or multiple times at the designated location on the sample 5 or loading pad, automatically. In particular, the engaging end 15 is lowered at a very slow rate until contact is made with the sample 5 or loading pad 12. Then the computer applies a programmed increasing DC current from source 17 to the load coil 11 of the actuator device 9, which forces the engaging end against the specimen 15, directly or indirectly, until a preselected junction loading or displacement level is reached and then the force is removed at the same or similar rate to unload the junction. During this loading and unloading cycle, the computer records the junction loading taken from the DC current (load) detector 27 and the engaging end displacement taken from the DC displacement detector 23. These values may be stored in the mass storage unit 31 for subsequent use in determining the various mechanical properties of sample 5 discussed below.

In accordance with an aspect of the invention comprising a method to continuously measure the stiffness of the sample 5 during the loading and unloading cycle, the system includes a means for applying a small mechanical vibrational force to the sample 5 including monitoring the resulting displacement relative to the applied force as a measure of the stiffness the sample 5. The force may be applied in the form of an oscillatory force (AC force), typically about $10.^{-8}$ N (Newton), by superimposing an AC current onto the DC drive current applied to the load coil 11. The frequency of the AC force applied is typically in the range of from 0.5 to 200 Hz for the system depicted in FIG. 1; however, depending on the design of the engaging end mounting assembly involved, the concept can work from about 0.5 Hz to 1 MHz. The amplitude of the oscillating force may be in the range of from about $10.^{-10}$ to 1 N, depending on the area of the contact.

This procedure may be accomplished by adding an AC signal generator 33 under control of the computer 19 to inject an AC signal into the output current signal of the current source 17 and detecting the resulting AC displacement by means of an AC displacement detector 35. The detector 35 may be a lock-in amplifier which is tuned to measure the amplitude of the AC displacement at the applied frequency together with the phase of the displacement signal relative to the applied signal. The amplitude and phase signals are digitized by the detector 35 and fed to separate inputs of the computer 19 for analysis or storage along with the DC force and displacement information during a loading and unloading cycle. The force-displacement response data can be provided as an output for use in ascertaining one or more mechanical properties of the material that the sample 5 is made from. Alternatively, computer 19 can perform the necessary calculations using the data and provide the one or more mechanical properties as an output.

A method is herein described to use experimentally acquired force-displacement or stiffness-displacement data to measure the elastic modulus and the residual stress of thin films in the physical shape of a sample supported with a portion in free space, for example, when supported at both ends in a doubly clamped bridge. As appreciated by those skilled in the art such data can also be used to ascertain other mechanical properties such as but not limited to creep, plastic deformation or yield strength to name but a few.

Using by way of example the sample 5 supported by spaced apart supports 6, in response to an applied load applied to the portion disposed in free space such as at the center of the sample 5 forming a bridge between end supports 6, the elastic deformation of the structure can be modeled according to the schematic illustration in FIG. 2, where, L is the full length of the sample bridge portion, P is the applied normal load, W is the length of the landing zone/pad along the long axis of the sample bridge portion, h is the measured normal deflection of the sample bridge portion, θ is the angle between the displaced and equilibrium position of the sample bridge portion, ΔI is the extension of the sample bridge portion, F is the the sum of the initial tensile or compressive force in the sample bridge portion (due to the residual stress) and the resolved component of the applied force, P, that acts perpendicular to the cross-sectional area of the sample bridge portion, $w_B$ is the width of the sample bridge portion, t is the thickness of the sample bridge portion, A is the cross-sectional area of the sample bridge portion (taken to be $w_B$ multiplied by t), S is the measured stiffness of the sample bridge portion, E is the elastic modulus of the sample bridge portion, $\sigma_r$ is the residual stress in the sample bridge portion, $\epsilon$ is the strain in the sample bridge portion, and where the known variables are L, W, $w_B$, and t, and the measured or controlled variables are P, h, and S.

Figure 3:
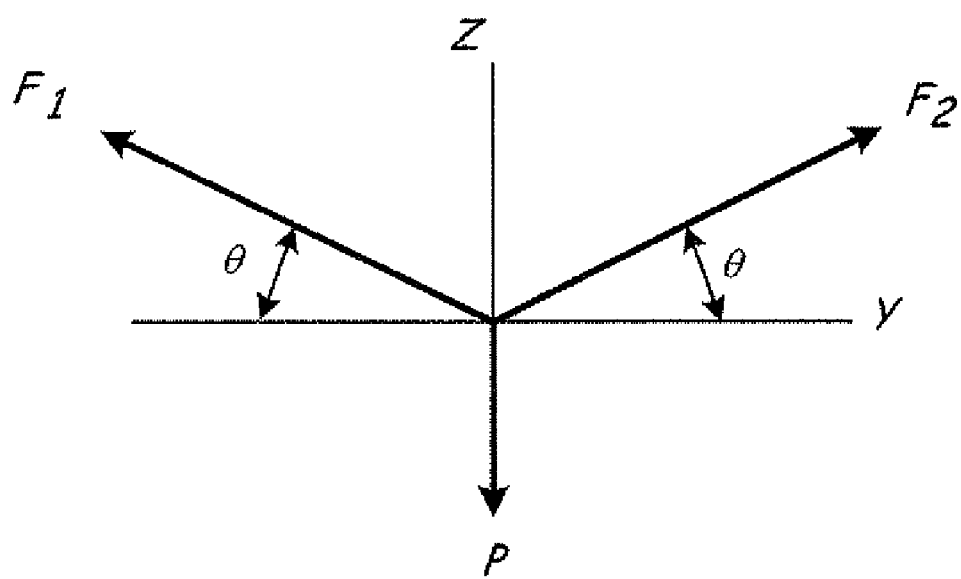
FIG. 3 is a free body diagram of the system of FIG. 3

The resulting free body diagram is illustrated in FIG. 3. Based on this simple model and its free body diagram, the load-displacement (P-h) relationship of the sample bridge portion is $$P = \frac{8AEh^3}{L(L-W)^2} - \frac{8A\sigma_r h^3}{(L-W)^3} + \frac{4A\sigma_r h}{L-W}. \tag{33}$$

Differentiating this expression with respect to the vertically imposed displacement yields the relationship between stiffness and displacement (S-h), $$S = \frac{\partial P}{\partial h} = \frac{24AEh^2}{L(L-W)^2} - \frac{24A\sigma_r h^2}{(L-W)^3} + \frac{4A\sigma_r}{L-W}. \tag{34}$$

By curve fitting experimentally acquired stiffness-displacement data according to the parabolic form of the theoretical relationship, $$y = k_2 h^2 + k_1 h + k_0, \tag{38}$$

the fit coefficients $k_0$ and $k_2$ can be used to determine both the elastic modulus and the residual stress in the spanning portion 5A. In particular, the relationships between the fit parameters and the properties of the bridge can be expressed as, $$\sigma_r = \frac{k_0(L-W)}{4A}, \text{ and} \tag{41}$$

$$E = \frac{L}{4A}\left[\frac{k_2(L-W)^2}{6} + k_0\right]. \tag{42}$$

It should be noted this embodiment is based on two assumptions of the model. First, it is assumed the supports 6 are rigid; and second, the bending moments at the juncture between the spanning portion 5A and the supports 6 and on either side of the landing zone 12 may be ignored. Nevertheless, other models in the open literature present the load-displacement relationship of the bridge, Equation (33), with additional terms that approximately account for bending and a finite post stiffness. These additional terms could be readily added to Equation (33), and therefore, incorporated into stiffness-displacement relationship, Equation (34), and the resulting equations, Equations (41) and (42). In the embodiment described, these additional terms are not included because they can add to the complexity of the modeling and the uncertainty of the test results in a manner that may be avoidable through careful design of the structure.

Figure 4:
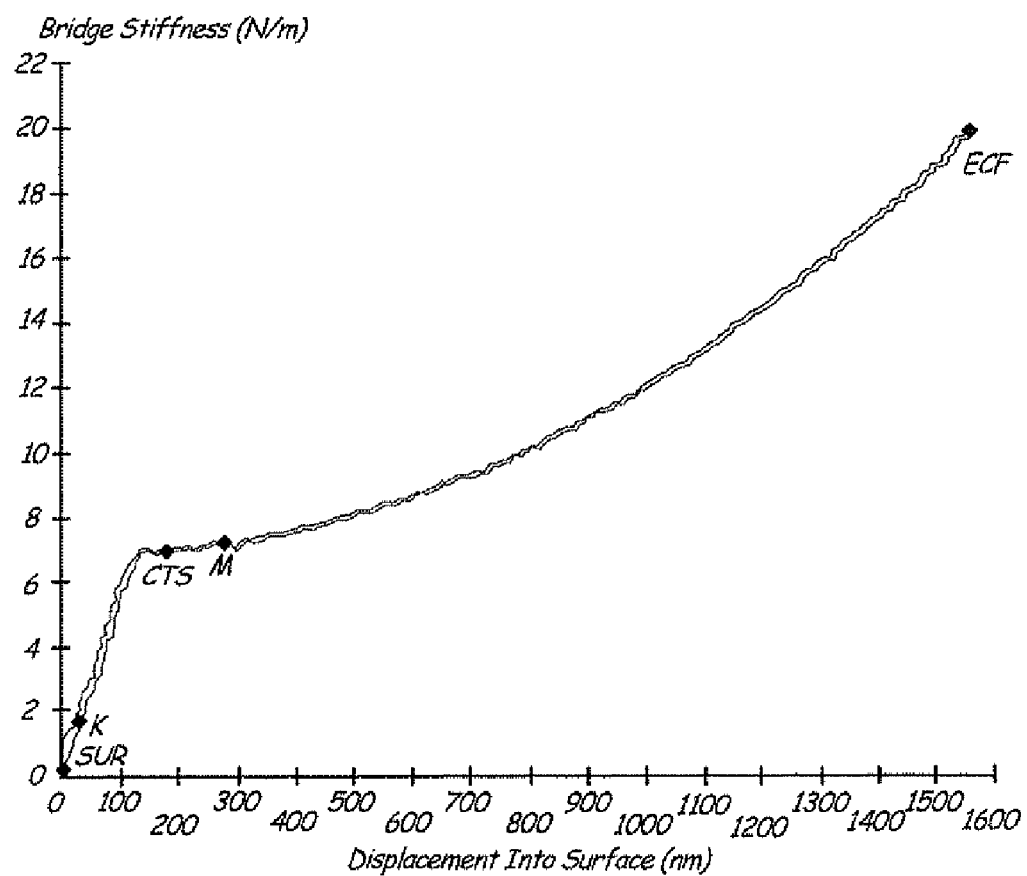
FIG. 4 illustrates experimentally measured stiffness-displacement data representing the elastic loading and unloading of a sample.

FIG. 4 illustrates experimentally acquired stiffness-displacement data on a doubly clamped bridge measuring 66 µm long by 8 µm wide by 65 nm thick. The data represent both the loading and unloading of three experiments performed at the center of the landing zone. The complete reversibility of the loading and unloading clearly demonstrates that the deformation is wholly elastic. In addition, the precision of the measurement is demonstrated by the excellent reproducibility of the three experiments. Filling the data beyond 140 nm to equation (38) and using the fit coefficients $k_0$, and $k_2$, the elastic modulus and the residual stress were determined according to equations (41) and (42).

Figure 5:
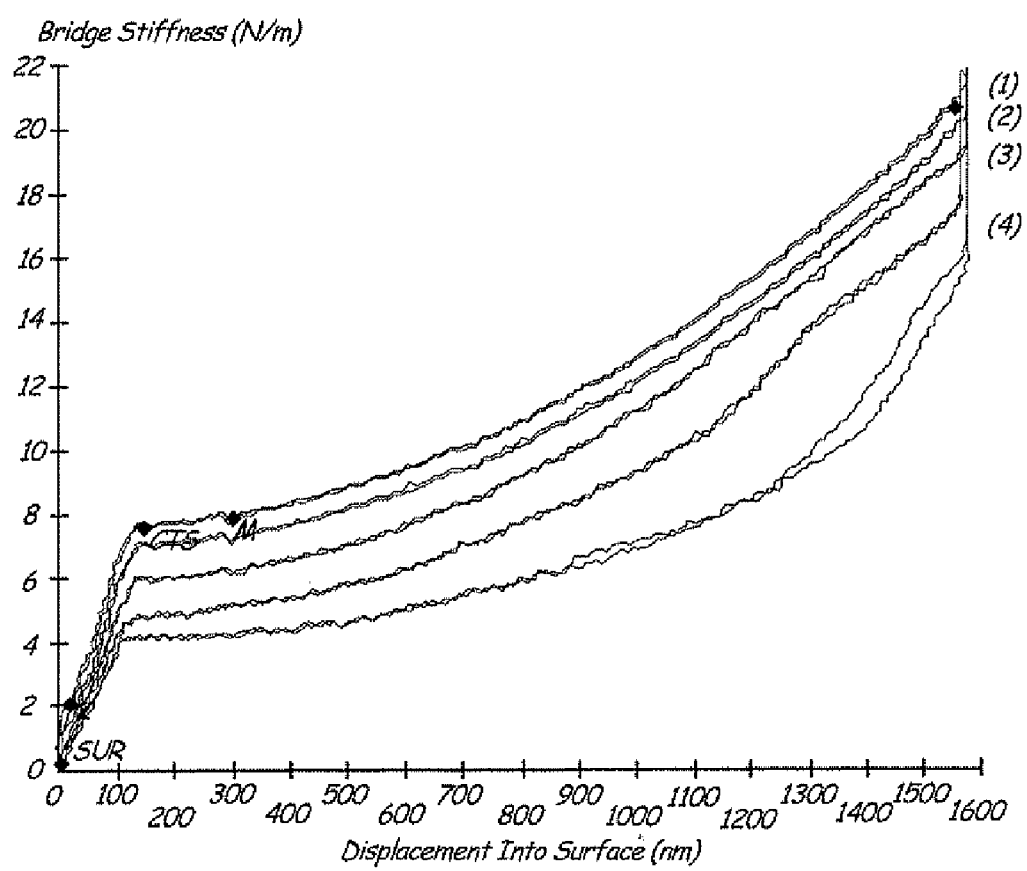
FIG. 5 illustrates experimentally measured stiffness-displacement data representing the elastic loading and unloading of a sample at selected locations along its width.

It should be noted, experimental observation indicates that the measured stiffness-displacement response of the spanning portion 5A is a strong function of the targeted test position along the short axis of the spanning portion 5A. For the purposes of this discussion, the short axis of the spanning portion 5A is taken to be the x-axis and the length of the spanning portion 5A is taken to be the y-axis. FIG. 5 shows the stiffness-displacement data from five experiments performed on a single sample bridge portion measuring 66 by 8 µm by 65 nm. Each experiment was performed at different x-axis locations on the landing zone 12. Keeping the y-axis position constant at each of the five test locations, the x-axis coordinate was varied by 1 µm intervals to both the left and right of the assumed center of the landing zone 12. FIG. 5 clearly illustrates the significant variability of the measured stiffness as a function of the selected x-axis test position. Moving the x-axis test position closer to the edge of the bridge by 1 and 2 µm (12.5 and 25% of the bridge width) produced measured stiffness approximately 16 and 40% lower than the measured stiffness at the center of the sample bridge portion. These lower stiffness measurements are most likely the result of performing the experiments close to the edge of the sample bridge portion, thereby twisting it as opposed to linearly displacing it.

Due to the small width of samples (e.g. 8 µm) and the need to target the center, another aspect is a method is provided to accurately determine the center of the bridge. Generally, this method includes deflecting the sample at selected positions across the sample portion 5 or landing pad 12 and ascertaining which location would realize the greatest measurement of stiffness. In one embodiment, this method includes calculating or determining the stiffness at each location; however, in other embodiments, the calculation need not be in units of stiffness, but rather a value related to stiffness.

Figure 6:
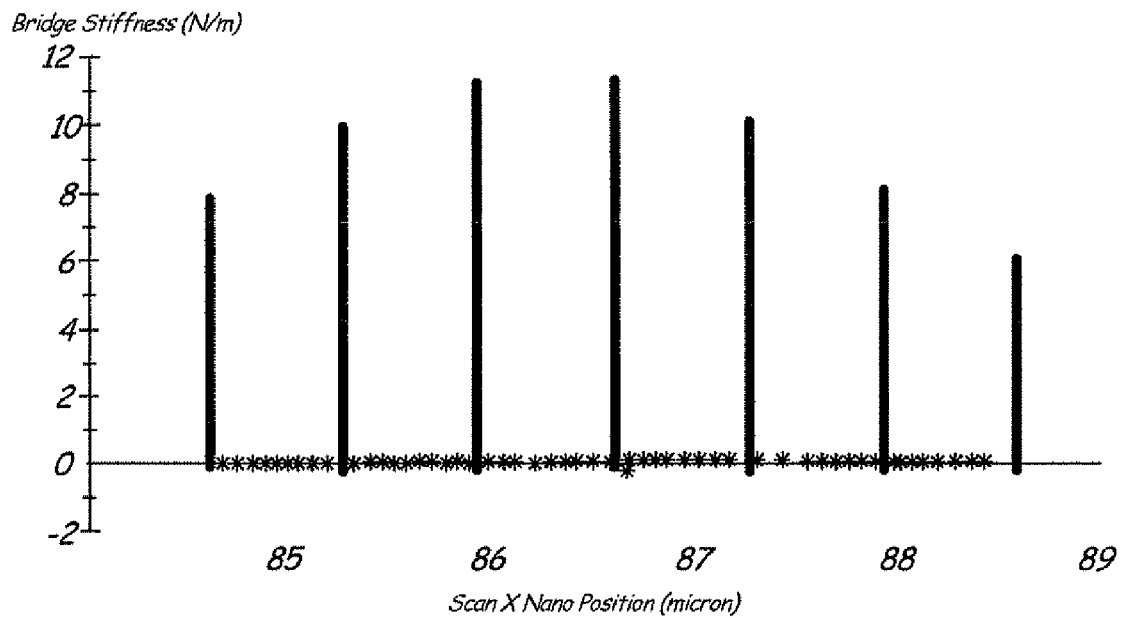
FIG. 6 illustrates stiffness as a function of position along a width of a sample.

Illustrating this procedure, FIG. 6 illustrates the stiffness as a function of position where each peak in stiffness represents one of seven locations across the x-axis of the landing zone of the sample 5. The seven peaks represent a change in the x-axis position of approximately 666 nm. The location that produces the highest measured stiffness, or a value related to the highest measured stiffness, is taken to be the center of the bridge. The stiffness-displacement experiment can then be performed at that location.

Unlike the response across the sample bridge portion, the measured stiffness-displacement response of the sample bridge portion generally does not exhibit any measurable functionality with the targeted test position along the long axis (y-axis) of the sample bridge portion. In other words, the elastic modulus and the residual stress are relatively insensitive to small changes in the y-axis test position of the center of the sample bridge portion.

It should also be noted that the data obtained to locate the center of the spanning portion 5A across its width can be used to obtain an indication or relationship of the sample's shear modulus and Poisson's ratio. For instance, using the data as represented by FIG. 6, curve fitting techniques such as fitting a parabola to the acquired data and taking the derivative of the resulting parabola equation can be used to find a "zero position" or center of the sample bridge portion. Each of the locations used to obtain the measured values of stiffness (e.g as represented by FIG. 6) can then be used relative to the zero position to obtain a change in distance from the zero position (h), which can be used (e.g. plotted) with the measured values of stiffness in order to obtain the relationship between shear modulus and Poisson's ratio.

In this exemplary embodiment, a simple model of the elastic deformation of thin films in the form of a doubly clamped bridge has been used to develop the theoretical stiffness-displacement relationship of the sample bridge portion. Applying the model to experimentally acquired stiffness-displacement data, the elastic modulus and the residual stress in the specimen film can be measured. Due to the geometry of the sample bridge portion, the measured stiffness-displacement response appears dependent on accurately targeting the center of the sample bridge portion along its short axis. The center position can be determined using a procedure that utilizes the measured stiffness (or value related thereto) to identify the stiffest location across the landing zone, which is then taken to be the center of the sample bridge portion along its short axis. Along the long axis of the sample bridge portion, the measured stiffness-displacement response is relatively insensitive to the selected test position. The mounting structure for the sample should be built as rigid as possible while the sample bridge portions should be long, thin, and narrow.

Unlike prior techniques that predict the elastic modulus and residual stress based on the relationship between experimentally acquired load and displacement data and the geometry of the sample bridge portion, the method herein described is based on the relationship between stiffness and displacement, Equation (34), as opposed to the relationship between load and displacement, Equation (33). The stiffness-displacement relationship provides improved results because stiffness can be experimentally measured using frequency specific techniques which improve the signal to noise ratio in comparison to broad band measurements of load and displacement.

The foregoing description is based on a membrane model. It treats the sample bridge portion as a membrane and therefore makes no attempt to account for bending at the supports or at the juncture between the engaging end and the sample bridge portion. In the alternative, a bending model can also be used. The bending model is very similar in its form to the membrane model, but as the name implies, it incorporates the bending moments at the supports and the juncture between the is engaging end and the sample bridge portion.

As provided above, the load-displacement relationship for the membrane model is $$P = \frac{8AEh^3}{L^3} - \frac{8A\sigma_r h^3}{L^3} + \frac{4A\sigma_r h}{L}, \qquad (44)$$

where P is the applied load, A is the cross-sectional area of the sample bridge portion, L is the length of the sample bridge portion, E is the elastic modulus, $\sigma_r$ is the residual stress and h is the normal deflection of the sample bridge portion. The $2^{nd}$ term of this expression only makes a significant contribution when the residual stress is large in comparison to the elastic modulus—most of the time it can be safely ignored.

The load-displacement relationship for the bending model is $$P = \frac{\pi^4 A E h^3}{8L^3} + \frac{\pi^4 A E t^2 h}{6L^3} + \frac{\pi^2 A \sigma_r h}{2L}, \qquad (45)$$

where t is the thickness of the sample bridge portion. In comparison to the membrane model, the first and third terms of this expression only differ in the value of the constants. The second term of this expression is the bending term, which is what is unique about this expression.

The stiffness-displacement relationship is helpful because the frequency specific technique used to experimentally measure the stiffness dramatically improves the signal to noise ratio in comparison to broad band measurements of load and displacement. Differentiating the previous equation with respect to h and using the Buckingham PI theorem to cast the resulting expression in a non-dimensional form, significant physical insight can be gained in determining how the geometry and properties of the bridge control how the deformation of the structure is accommodated. The non-dimensional form of the stiffness-displacement relationship of the bending model is $$\frac{SL}{AE} = \frac{3\pi^4}{8}\left(\frac{h}{L}\right)^2 + \frac{\pi^4}{6}\left(\frac{t}{L}\right)^2 + \frac{\pi^2}{2}\frac{\sigma_r}{E}. \qquad (46)$$

The non-dimensional PI groups are $$\left(\frac{h}{L}\right)^2, \left(\frac{t}{L}\right)^2, \text{ and } \left(\frac{\sigma_r}{E}\right).$$

The utility of these PI groups is that they make it possible to identify very useful boundaries. The PI group from the $1^{st}$ term, $$\left(\frac{h}{L}\right)^2,$$

increases as the structure is vertically displaced during an experiment. Thus this term becomes more and more significant as the vertical displacement increases. The remaining two, $$\left(\frac{t}{L}\right)^2 \text{ and } \left(\frac{\sigma_r}{E}\right),$$

are both fixed for a given structure. Thus their contribution is independent of the vertical displacement. In comparing the ratio of $$\left(\frac{\sigma_r}{E}\right) \text{ and } \left(\frac{t}{L}\right)^2,$$

it is clear that bending (the second term of the equation) can be safely ignored in the limit that $$\left(\frac{\sigma_r}{E}\right) \gg \left(\frac{t}{L}\right)^2.$$

In comparing the ratio of $$\left(\frac{\sigma_r}{E}\right) \text{ and } \left(\frac{h}{L}\right)^2,$$

it is clear that the initial portion of the experiment is dominated by either the residual stress or a combination of the residual stress and bending. As the ratio of $$\left(\frac{h}{L}\right)^2$$

continues to increase during an experiment, the contribution of the residual stress becomes less and less. From these relationships and data obtained using the procedure provided above, mechanical properties such as but not limited to elastic modulus and residue stress can be obtained for the sample.

Derivation of Relations for Membrane Model

Although not necessary for practicing the method/system herein described, the derivation of the relationship between the stiffness of the sample bridge portion and the elastic modulus of the sample bridge portion and the residual stress in the sample bridge portion is provided. The free body diagram in FIG. 3 assumes the load is applied to the center of the sample bridge portion. By summing the forces in the y direction, it is clear that the resolved component of P must necessarily be the same on both sides of the sample bridge portion.

$$\stackrel{+}{\rightarrow} \sum F_y = 0 \Rightarrow F_2 \cos\theta - F_1 \cos\theta = 0 \Rightarrow F_2 = F_1 = F \quad (1)$$

By summing the forces in the z direction, F can be defined in terms of θ and the applied force, P.

$$\stackrel{+}{\uparrow} \sum F_z = 0 \Rightarrow F\sin\theta + F\sin\theta - P = 0 \Rightarrow 2F\sin\theta - P = 0 \Rightarrow F = \frac{P}{2\sin\theta} \quad (2)$$

In order to utilize this expression, the angle θ, or the entire term, sin θ, must be defined using the known or measured variables. Since the angle is dependent on the extension of the sample bridge portion, one can start by defining the strain in the sample bridge portion.

From the free body diagram in FIG. 3, the strain in the sample bridge portion is $$\varepsilon = \frac{\Delta L}{L} = \frac{2\left(\frac{L-W}{2} + \Delta l\right) - 2\left(\frac{L-W}{2}\right)}{L} = \frac{2\Delta l}{L} \quad (3)$$

In order to utilize this expression, Δl, the extension of the sample bridge portion, must be defined in terms of the known or measured variables.

$$\sin\theta = \frac{opp}{hyp} = \frac{h}{(L-W)/2 + \Delta l} = \frac{2h}{L - W + 2\Delta l} \quad (4)$$

$$\tan\theta = \frac{opp}{adj} = \frac{h}{(L-W)/2} = \frac{2h}{L-W} \quad (5)$$

$$\theta = \tan^{-1}\left(\frac{2h}{L-W}\right) \quad (6)$$

Combining equations (4) and (6), $$\sin\theta = \sin\left[\tan^{-1}\left(\frac{2h}{L-W}\right)\right] = \frac{2h}{L - W + 2\Delta l} \quad (7)$$

$$L - W + 2\Delta l = \frac{2h}{\sin\left[\tan^{-1}\left(\frac{2h}{L-W}\right)\right]} \quad (8)$$

$$2\Delta l = \frac{2h}{\sin\left[\tan^{-1}\left(\frac{2h}{L-W}\right)\right]} - (L - W) \quad (9)$$

$$\Delta l = \frac{h}{\sin\left[\tan^{-1}\left(\frac{2h}{L-W}\right)\right]} - \frac{(L-W)}{2} \quad (10)$$

Now the Δl in equation (3) can be replaced by equation (10) and simplified.

$$\varepsilon = \frac{2\left[\dfrac{h}{\sin\left[\tan^{-1}\left(\frac{2h}{L-W}\right)\right]} - \dfrac{(L-W)}{2}\right]}{L} \quad (11)$$

$$\varepsilon = \frac{\dfrac{2h}{\sin\left[\tan^{-1}\left(\frac{2h}{L-W}\right)\right]} - (L - W)}{L} \quad (12)$$

$$\varepsilon = \frac{\dfrac{2h}{\sin\left[\tan^{-1}\left(\frac{2h}{L-W}\right)\right]} - L + W}{L} \quad (13)$$

The strain in the sample bridge portion (considering both sides):

$$\varepsilon = \frac{2h}{\sin\left[\tan^{-1}\left(\frac{2h}{L-W}\right)\right]L} + \frac{W}{L} - 1 \quad (14)$$

Assuming the deformation of the sample bridge portion is elastic, the stress in the sample bridge portion is $$\sigma = \frac{F}{A} = E\varepsilon + \sigma_r \quad (15)$$

$$F = A(E\varepsilon + \sigma_r) \quad (16)$$

Recalling equation (2), $$F = \frac{P}{2\sin\theta} = A(E\varepsilon + \sigma_r) \quad (17)$$

$$P = 2A(E\varepsilon + \sigma_r)\sin\theta \quad (18)$$

Now substitute equation (14) for the $\varepsilon$, but note that equation (14) has been simplified by using equation (7) to express the relation in terms of $\sin\theta$.

$$P = 2A\left[E\left(\frac{2h}{L\sin\theta} + \frac{W}{L} - 1\right) + \sigma_r\right]\sin\theta \quad (19)$$

$$P = 2A\left[\frac{2Eh}{L\sin\theta} + \frac{EW}{L} - E + \sigma_r\right]\sin\theta \quad (20)$$

$$P = 2A\left(\frac{2Eh}{L} + \frac{EW}{L}\sin\theta - E\sin\theta + \sigma_r\sin\theta\right) \quad (21)$$

$$P = \frac{4AEh}{L} + \frac{2AEW}{L}\sin\theta - 2AE\sin\theta + 2A\sigma_r\sin\theta \quad (22)$$

As previously noted, recall from equation (7), $$\sin\theta = \sin\left[\tan^{-1}\left(\frac{2h}{L-W}\right)\right]$$

In order to simplify the differentiation of the P-h relationship (Eq. (22)), a trigonometric series approximation is used in place of the term $\sin\theta$.

$$\tan^{-1}(x) = x - \frac{1}{3}x^3 + \frac{1}{5}x^5 - \ldots \text{ for } x^2 < 1 \quad (23)$$

$$\sin(x) = x - \frac{x^3}{3!} + \frac{x^5}{5!} - \frac{x^7}{7!} + \ldots \quad (24)$$

$$\sin\left(x - \frac{x^3}{3}\right) = \left(x - \frac{x^3}{3}\right) - \frac{\left(x - \frac{x^3}{3}\right)^3}{3!} \quad (25)$$

$$\sin\left(x - \frac{x^3}{3}\right) = x - \frac{x^3}{3} - \left(\frac{\frac{-x^9}{27} + \frac{x^7}{3} - x^5 + x^3}{6}\right) \quad (26)$$

$$\sin\left(x - \frac{x^3}{3}\right) = x - \frac{x^3}{3} - \frac{x^3}{6} \quad (27)$$

$$\sin\left(x - \frac{x^3}{3}\right) = x - \frac{x^3}{2} \quad (28)$$

The series approximation produces an error of less than 1% in the evaluation of $\sin\theta$ when $\theta < 22$ degrees (this corresponds to normal displacements of the sample bridge portion that are approximately 20% of its length). However, as this small error percolates through to the final calculations of E and $\sigma_r$, the error becomes amplified. This problem can be solved by either: 1) limiting the normal displacement of the sample bridge portion to approximately 2.5% of the sample bridge portion length, or 2) adding another term to the series expansion, i.e. equation 26.

Using equation 28, the approximation is, $$\sin\theta = \quad (29)$$

$$\sin\left[\tan^{-1}\left(\frac{2h}{L-W}\right)\right] = \frac{2h}{L-W} - \frac{\left(\frac{2h}{L-W}\right)^3}{2} = \frac{2h}{L-W} - \frac{4h^3}{(L-W)^3}$$

Now replace the $\sin\theta$ term in equation (22) with equation (29) and simplify, $$P = \frac{4AEh}{L} + \frac{2AEW}{L}\left(\frac{2h}{L-W} - \frac{4h^3}{(L-W)^3}\right) - \quad (30)$$
$$2AE\left(\frac{2h}{L-W} - \frac{4h^3}{(L-W)^3}\right) + 2A\sigma_r\left(\frac{2h}{L-W} - \frac{4h^3}{(L-W)^3}\right)$$

$$P = \frac{4AEH}{L} + \frac{4AEWh}{L(L-W)} - \frac{8AEWh^3}{L(L-W)^3} - \quad (31)$$
$$\frac{4AEh}{L-W} + \frac{8AEh^3}{(L-W)^3} + \frac{4A\sigma_r h}{L-W} - \frac{8A\sigma_r h^3}{(L-W)^3}$$

$$P = \frac{4AEh}{L} + \frac{4AEh}{L-W} - \frac{4AEh}{L} - \left(\frac{8AEh^3}{(L-W)^3} - \frac{8AEh^3}{L(L-W)^2}\right) - \quad (32)$$
$$\frac{4AEh}{L-W} + \frac{8AEh^3}{(L-W)^3} + \frac{4A\sigma_r h}{L-W} - \frac{8A\sigma_r h^3}{(L-W)^3}$$

The final load-displacement relationship written in terms of the geometry and properties of the sample bridge portion is $$P = \frac{8AEh^3}{L(L-W)^2} - \frac{8A\sigma_r h^3}{(L-W)^3} + \frac{4A\sigma_r h}{L-W}. \quad (33)$$

Differentiating Eq. (33) with respect to displacement yields $$S = \frac{\partial P}{\partial h} = \frac{24AEh^2}{L(L-W)^2} - \frac{24A\sigma_r h^2}{(L-W)^3} + \frac{4A\sigma_r}{L-W}. \quad (34)$$

Plotting the experimentally measured S vs. h and fitting the data according to $$y = k_2 h^2 + k_1 h + k_0 \quad (38)$$

produces the three fit coefficients $k_0$, $k_1$, and $k_2$ where $$k_0 = \frac{4A\sigma_r}{L-W} \quad (39)$$

$$k_2 = \frac{24AE}{L(L-W)^2} - \frac{24A\sigma_r}{(L-W)^3} \quad (40)$$

Solving Eq. (39) for the residual stress, $$\sigma_r = \frac{k_0(L-W)}{4A} \quad (41)$$

Replacing the residual stress in Eq. (40) with Eq. (41) and solving for the elastic modulus.

$$E = \frac{L}{4A}\left[\frac{k_2(L-W)^2}{6} + k_0\right]. \quad (42)$$

Although the subject matter has been described in language specific to structural features and/or methodological acts, it is to be understood that the subject matter defined in the appended claims is not limited to the specific features or acts described above as has been held by the courts. Rather, the specific features and acts described above are disclosed as example forms of implementing the claims. Furthermore, the analytic modeling techniques should not be limited to those discussed above. In particular, alternative membrane and bending models can be used. Likewise, other forms of models (e.g. numerical) can be used.

What is claimed is:

1. A method for testing a thin specimen sample, the method comprising:
   supporting the sample with a spanning portion spanning in an environment between at least three points not in a line, wherein the points are fixed relative to each other, and wherein the spanning portion is capable of displacement relative to the points;
   applying an oscillating mechanical excitation at at least one frequency and at at least one known amplitude to the spanning portion;
   applying at least one other mechanical excitation to the spanning portion independently of the oscillating mechanical excitation;
   obtaining a first force-displacement response of the spanning portion of the sample relative to the applied oscillating mechanical excitation, and obtaining a second force-displacement response of the spanning portion of the sample relative to the at least one other mechanical excitation, wherein the first force-displacement response comprises an amplitude response and/or phase response relative to the applied oscillating mechanical excitation; and
   providing an indication of at least one mechanical property of the material from which the specimen is made based on the first force-displacement response.

2. The method according to claim 1 and further comprising providing an indication of at least one mechanical property of the material from which the specimen is made based on the force-displacement responses.

3. The method of claim 2 wherein providing the indication comprises providing an indication of at least one of residue stress and Poisson's ratio of the sample.

4. The method of claim 2 wherein providing the indication includes determining the mechanical property based on a membrane model.

5. The method of claim 2 wherein providing the indication includes determining the mechanical property based on a bending model.

6. The apparatus of claim 2 wherein providing the indication includes determining the mechanical property based on a numerical model.

7. The method of claim 1 wherein the environment does not impart stress on to the spanning portion when the spanning portion is displaced.

8. The method of claim 1 wherein the environment comprises a fluid.

9. The method of claim 8 wherein the environment comprises at least one gas.

10. The method of claim 8 wherein the environment comprises at least one liquid.

11. The method of claim 1 wherein obtaining the force-displacement response of the oscillating mechanical excitation includes applying a force to the spanning portion and measuring corresponding displacement thereof.

12. The method of claim 1 wherein obtaining the force-displacement response of the oscillating mechanical excitation includes displacing the spanning portion and measuring a corresponding force to effectuate the displacement.

13. The method of claim 1 wherein obtaining the force-displacement response of the at least one other mechanical excitation includes applying a force to the spanning portion and measuring corresponding displacement thereof.

14. The method of claim 1 wherein obtaining the force-displacement response of the at least one other mechanical excitation includes displacing the spanning portion and measuring a corresponding force to effectuate the displacement.

15. The method of claim 1 wherein the at least one other excitation is static for a selected time period.

16. The method of claim 1 wherein the at least one other excitation varies during a time period.

17. The method of claim 1 wherein applying the oscillating mechanical excitation comprises a plurality of frequencies each having a selected amplitude, wherein the plurality of frequencies are applied simultaneously.

18. The method of claim 1 wherein applying the oscillating mechanical excitation comprises applying oscillating mechanical excitation that has a frequency that varies over a time period.

19. The method of claim 1 wherein applying the oscillating mechanical excitation comprises applying oscillating mechanical excitation that has a frequency that varies over a time period at discrete frequencies.

20. The method of claim 1 wherein applying the oscillating mechanical excitation comprises applying oscillating mechanical excitation where the at least one amplitudes varies over a selected time period.

21. The method of claim 1 wherein the spanning portion is in tension loading only due to application of the mechanical excitations.

22. The method of claim 1 wherein the spanning portion is in tension and torsional loading due to application of the mechanical excitations.

23. The method of claim 1 and further comprising providing an indication of stiffness relative to displacement of the portion of the sample capable of displacement.

24. The method of claim 1 wherein supporting the sample comprises supporting the sample at opposite ends with the spanning portion of the sample capable of displacement located between the opposite ends.

25. The method of claim 24 wherein spanning portion includes a support frame about a perimeter of the spanning portion.

26. An apparatus for ascertaining a property of a thin specimen sample comprising:
   a sample support system adapted to support a sample such that a spanning portion of the sample spans in an environment between at least three points not in a line, wherein the points are fixed relative to each other, and wherein the spanning portion is capable of displacement relative to the points;

a tip adapted to apply mechanical excitation to the spanning portion of the sample;

an actuator coupled to the support system and/or the tip to cause relative displacement of the tip and the support system to apply the mechanical excitation;

a sensor configured to measure a mechanical response of the sample; and a controller operably coupled to the actuator and the sensor, the controller being configured to apply an oscillating mechanical excitation at at least one frequency and at at least one known amplitude to the spanning portion, and applying at least one other mechanical excitation to the spanning portion independently of the oscillating mechanical excitation, wherein the controller is configured to measure an amplitude response and/or phase response of the mechanical response of the sample relative to the applied oscillating mechanical excitation, and wherein the controller is configured to provide an indication of at least one mechanical property of the material from which the sample is made based on the first force-displacement response.

27. The apparatus of claim 26 wherein the actuator further comprises an electric actuator.

28. The apparatus of claim 26 wherein the actuator further comprises a load coil.

29. The apparatus of claim 26 wherein the actuator further comprises an electrostatic actuator.

30. The apparatus of claim 26 wherein the actuator further comprises a piezoelectric actuator.

31. The apparatus of claim 26 wherein said sensor comprises a capacitive displacement gage.

32. The apparatus of claim 26 wherein said sensor comprises an electromagnetic based displacement gage.

33. The apparatus of claim 26 wherein the oscillating mechanical excitation comprises a plurality of frequencies each having a selected amplitude, and wherein the plurality of frequencies are applied simultaneously.

34. The apparatus of claim 26 wherein the oscillating mechanical excitation comprises a frequency that varies over a time period.

35. The apparatus of claim 26 wherein the oscillating mechanical excitation comprises a frequency that varies over a time period at discrete frequencies.

36. The apparatus of claim 26 wherein the oscillating mechanical excitation comprises at least one amplitude that varies over a selected time period.

37. The apparatus of claim 26 wherein the controller is configured to provide an indication of stiffness relative to displacement based on the measured mechanical response of the sample.

38. The apparatus of claim 26 wherein the controller is configured to provide an indication of at least one mechanical property of the material from which the specimen is made based on the mechanical response of the sample.

39. The apparatus of claim 38 wherein the controller is configured to provide the mechanical property based on a membrane model.

40. The apparatus of claim 38 wherein the controller is configured to provide the mechanical property based on a membrane model.

41. The apparatus of claim 38 wherein the controller is configured to provide the mechanical property based on a numerical model.

* * * * *

UNITED STATES PATENT AND TRADEMARK OFFICE
CERTIFICATE OF CORRECTION

PATENT NO. : 7,441,465 B2  Page 1 of 1
APPLICATION NO. : 11/757076
DATED : October 28, 2008
INVENTOR(S) : Oliver et al.

It is certified that error appears in the above-identified patent and that said Letters Patent is hereby corrected as shown below:

In column 15, line 65, in Claim 6, delete "apparatus" and insert -- method --, therefor.

Signed and Sealed this

Fourteenth Day of April, 2009

JOHN DOLL
*Acting Director of the United States Patent and Trademark Office*